(12) United States Patent
Ren et al.

(10) Patent No.: US 12,037,612 B2
(45) Date of Patent: Jul. 16, 2024

(54) HIGH THROUGHPUT REACTION ASSEMBLY

(71) Applicant: New England Biolabs, Inc., Ipswich, MA (US)

(72) Inventors: Guoping Ren, Danvers, MA (US); Yan Xu, Hamilton, MA (US); Dong Ma, Ipswich, MA (US); Nicole Nichols, Reading, MA (US)

(73) Assignee: New England Biolabs, Inc., Ipswich, MA (US)

( * ) Notice: Subject to any disclaimer, the term of this patent is extended or adjusted under 35 U.S.C. 154(b) by 50 days.

(21) Appl. No.: 17/936,144

(22) Filed: Sep. 28, 2022

(65) Prior Publication Data

US 2023/0013384 A1  Jan. 19, 2023

Related U.S. Application Data

(62) Division of application No. 16/286,040, filed on Feb. 26, 2019, now abandoned.

(60) Provisional application No. 62/637,029, filed on Mar. 1, 2018.

(51) Int. Cl.
| | |
|---|---|
| *C12Q 1/6806* | (2018.01) |
| *C12N 9/12* | (2006.01) |
| *C12Q 1/48* | (2006.01) |
| *C12Q 1/6816* | (2018.01) |
| *C12Q 1/6844* | (2018.01) |
| *C12Q 1/6851* | (2018.01) |
| *C12Q 1/686* | (2018.01) |

(52) U.S. Cl.
CPC .......... *C12N 9/1276* (2013.01); *C12Q 1/48* (2013.01); *C12Q 1/6806* (2013.01); *C12Q 1/6816* (2013.01); *C12Q 1/6846* (2013.01); *C12Q 1/6851* (2013.01); *C12Q 1/686* (2013.01); *C12Q 2521/107* (2013.01); *C12Q 2521/119* (2013.01); *C12Q 2527/125* (2013.01); *C12Q 2527/137* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 6,365,375 | B1 | 4/2002 | Dietmaier |
| 7,659,100 | B2 | 2/2010 | Born |
| 8,759,061 | B1 | 6/2014 | Marx |
| 9,034,606 | B2 | 5/2015 | Tanner et al. |
| 2012/0164654 | A1 | 6/2012 | Nakabayashi et al. |
| 2015/0104797 | A1 | 4/2015 | Fu |

FOREIGN PATENT DOCUMENTS

| | | |
|---|---|---|
| EP | 3533881 B1 | 8/2021 |
| WO | 2011039425 A1 | 4/2011 |
| WO | 2015162102 A1 | 10/2015 |

OTHER PUBLICATIONS

Souaze et al. Biotechniques vol. 21, pp. 280-285, Aug. 1996.*
Patton, et al. (2017) NEB expressions, Issue I, 2-5.
Hall, et al. (2013) PLOS One 8: e73845.
Fout, et al., Applied and Environmental Microbiology, 69, 6, 3158-3164, 2003.
Okimoto, et al., Biotechniques, 21, 1, 20-26, 1996.

* cited by examiner

*Primary Examiner* — Richard G Hutson
(74) *Attorney, Agent, or Firm* — New England Biolabs, Inc

(57) ABSTRACT

Provided herein is a reverse transcriptase mixture comprising a reverse transcriptase and a colored dye at a concentration in the range of 0.003%-1% (v/w). The colored dye may be visually observed during transfer of the mix from one vessel to another and addition of the mix to another mix can be confirmed by eye by observing the colored dye.

6 Claims, 9 Drawing Sheets

(9 of 9 Drawing Sheet(s) Filed in Color)

HIGH THROUGHPUT REACTION ASSEMBLY

CROSS REFERENCE

This application is a divisional application of U.S. application Ser. No. 16/286,040, filed Feb. 26, 2019, which claims priority from U.S. Provisional Application 62/637,029 filed on Mar. 1, 2018, herein incorporated by reference.

BACKGROUND

Multi-pipetting or single pipetting of small amounts of reagent is an intrinsic part of modern molecular biology. The robot or handler sets a reagent volume for the pipette(s) which are then supposed to pick up the predetermined amount of fluid. Unfortunately, this does not always occur, and variable volumes of reagent are picked up and inserted into reaction tubes. Because the fluid is transparent generally, the discrepancies often go unnoticed and have an effect on the results. It would be desirable to detect variations in fluid-fill in a manner that did not negatively impact the reaction.

Many techniques including Next-Generation sequencing now commonly require a series of reaction steps to manipulate the starting nucleic acid material for quantitative amplification and/or for sequencing. It would be desirable to be able to track one or more of these reactions.

SUMMARY

Provided herein is a mixture comprising a reverse transcriptase (RT), and a colored dye at a concentration that does not inhibit the reverse transcriptase activity (identified herein as a "reverse transcriptase mixture" or "reverse transcriptase mix"). The colored dye may be visually observed during transfer of the reverse transcriptase mix (or another mixture comprising it) from one vessel to another; and the addition of a volume of the reverse transcriptase mix (or another mixture comprising it) to another vessel, optionally containing a second mix, can be confirmed by eye by observing the colored dye.

In some embodiments, the reverse transcriptase mixture may comprise: (a) a reverse transcriptase; and (b) a colored dye having a concentration in the range of 0.003% to 1% (w/v). The colored dye may be one or a combination of xylene cyanol, tartrazine, or xylene cyanol and tartrazine (Sigma-Aldrich, St. Louis, MO).

In some embodiments, the reverse transcriptase may be present in the mixture at a concentration of at least 2 units/ul or at least 10 units/ul (e.g., in the range of 2 to 400 units/ul, such as 10 to 100 units/up.

In some embodiments, the reverse transcriptase mixture may further comprise glycerol or other equivalent inert high-density material such as ficoll, polysucrose, dextran or polyethylene Glycol (PEG), e.g., at a concentration in the range of 5% to 80% v/v. The use of the term "glycerol" herein can be deemed interchangeable with other equivalent materials having the same properties such as ficoll, dextran, polysucrose or polyethylene glycol. The reverse transcriptase mixture may additionally include a buffer. The reverse transcriptase mixture may additionally include one or more other components selected from dNTPs, nucleic acid primers, RNase inhibitors, and DNA adaptors, for example.

A kit is also provided. In some embodiments, the kit may include a reverse transcriptase and a colored dye, each as described herein, wherein the reverse transcriptase and colored dye are in the same container or separate containers, and the colored dye is at a concentration in the range of 0.003% to 1% (w/v). If the reverse transcriptase and the colored dye are in separate containers of the kit, they are suitable for combining to form a reverse transcriptase mixture as described herein. The kit may further comprise one or more of buffer, glycerol or equivalent, dNTPs, nucleic acid primers, adaptors, and an RNAse inhibitor, which may be in the same container with one or both of the reverse transcriptase and the colored dye or may be in one or more separate containers.

Methods are also provided. In some embodiments, the method may include: adding an aliquot from the reverse transcriptase mixture characterized by a dye dependent color described above to one or more reagents for complementary DNA (cDNA) synthesis, but not including template single strand nucleic acid, resulting in a colored cDNA synthesis mix (also described herein as a supermix); and confirming that the reverse transcriptase mixture has been added to the reagents for cDNA synthesis by visually observing the transferred color of the cDNA synthesis mix, or visually detecting the color of a bead in the cDNA synthesis mix (e.g. at or towards the bottom of a reaction tube containing the cDNA synthesis mix). The method may further comprise combining an aliquot of the colored cDNA synthesis mix with a first uncolored receiving mix containing a template single strand nucleic acid (e.g. DNAS or RNA), to produce a colored cDNA reaction mix; incubating the cDNA reaction mix to produce a cDNA product; and then adding a specific volume of the colored cDNA reaction mix comprising the cDNA product into a second uncolored receiving mix. The method may comprise visually observing the aliquot of the reverse transcriptase mixture and/or cDNA synthesis mix, or the specific volume of the cDNA reaction mix, such as in a series of micropipette tips optionally on a multi sample handler. Alternatively, or in addition, the method may comprise confirming that the cDNA synthesis mix has been combined with the first receiving mix and/or that the cDNA reaction mix has been added to the second receiving mix, by observing visually the addition of the colored dye from the cDNA synthesis mix and/or the cDNA reaction mix in the first and/or second receiving mix, respectively; and/or by detecting or observing the formation of a visually detectable bead in the receiving reaction mix (e.g. at or towards the bottom of a reaction tube containing the receiving reaction mix).

In some embodiments, a method is provided that includes: (a) combining an aliquot of a primary mix, wherein the primary mix comprises or consists of (i) the reverse transcriptase mixture or (ii) the cDNA synthesis mix described herein, with a first receiving mix containing a template single strand nucleic acid (e.g. RNA), to produce a cDNA reaction mix; (b) incubating the cDNA reaction mix to produce a cDNA product; and then (c), after (b), adding a specific volume of the cDNA reaction mix comprising the cDNA product into a second receiving mix. The method may further comprise visually observing the aliquot of the primary mix or the specific volume of the cDNA reaction mix, such as in a series of micropipette tips optionally on a multi sample handler. Alternatively, or in addition, the method may comprise confirming that the primary mix has been combined with the first receiving mix and/or that the cDNA reaction mix has been added to the second receiving mix, by observing visually the addition of the colored dye from the primary mix and/or the cDNA reaction mix in the first and/or second receiving mix, respectively; and/or by detecting or observing the formation of a visually detectable bead in the receiving reaction mix (e.g. at or towards the bottom of a reaction tube containing the receiving reaction mix).

In these embodiments, the visible colored bead from the primary mix containing glycerol or equivalent has a greater density than the buffer in the receiving reaction mix or the cDNA synthesis mix, in which case the visible colored bead is observed at or towards the bottom of a reaction tube containing the receiving reaction mix or the cDNA synthesis mix.

In some embodiments, the second receiving mix may comprise at least polymerase chain reaction (PCR) primers, dNTPs, and Taq polymerase, and addition of cDNA reaction mix comprising the cDNA product to the second receiving mix produces a PCR reaction mixture, and the method further comprises incubating the PCR reaction mixture to produce a PCR product.

In these embodiments, the colored dye in the reverse transcriptase mixture has been diluted out in the resulting PCR reaction mixture, so that its concentration is not inhibitory to the Taq polymerase in the PCR reaction. In some embodiments, the colored dye may be present in the PCR reaction mixture at a concentration of less than 0.007%, such as less than 0.005%, or less than 0.001%.

In some embodiments, the PCR reaction may be a quantitative polymerase chain reaction (qPCR) reaction.

In preferred embodiments, a single color resulting from one or more dyes is used throughout multiple transfers from the primary mix to one or more of receiving mixes in parallel and/or in series.

Other embodiments may be described below.

BRIEF DESCRIPTION OF THE FIGURES

The patent or application file contains at least one figure executed in color. Copies of this patent or patent application publication with color figures will be provided by the Office upon request and payment of the necessary fee.

Some aspects of the invention may be best understood from the following detailed description when read in conjunction with the accompanying drawings. It is emphasized that, according to common practice, the various features of the drawings may not be to scale. Indeed, the dimensions of the various features may be arbitrarily expanded or reduced for clarity. Included in the drawings are the following figures.

FIG. 1A-1G shows two samples with different amounts of dye in an aqueous buffer.

In FIG. 1A, 0.0160% xylene cyanol is included in the mix.
In FIG. 1B, 0.0032% xylene cyanol is included in the mix.

FIG. 2A shows six tubes each with a 0.0032% xylene cyanol dye in a cDNA synthesis mix and 6 tubes with no dye (left side).

FIGS. 2B and 2C each show pipette tips which should have the same volume (1 ul) of a solution containing 0.0032% xylene cyanol (on right) with the same solution with no dye on the left. The dye provides a rapid easy assessment of fluid volume compared with the left side.

FIG. 2D shows six tubes with 0.0154% tartrazine dye (right) and no dye (left).

FIG. 2E show pipette tips which allegedly have the same volume (1 ul) in each tip. The tartrazine dye provides a rapid easy assessment of fluid volume compared with the left side.

FIG. 2F shows six tubes each with a buffer containing 0.0077% tartrazine+0.0077% xylene cyanol dye (right) and no dye (left) colored green.

FIG. 2G show pipette tips which should have the same volume (1 ul). The tartrazine and xylene cyanol dye mixture provides a rapid easy assessment of fluid volume compared with the left side. The alleged same volumes appear very uneven emphasizing the utility of dye in the solution.

From left to right:

Tubes 1 and 2 contain no dye in cDNA reaction mix and no dye in qPCR master mix

In Tubes 3 and 4, 1 ul of a cDNA reaction mix containing 0.0032% blue dye was added to 19 ul qPCR master mix without dye. Colored beads were visible at the base of the receiving tube formed from the inert dense glycerol or equivalent, and the cDNA reaction mix.

In Tubes 5 and 6, 1 ul of the cDNA reaction mix with no dye was added to a qPCR mix with a 0.0003% dye.

Tubes 7 and 8 contain 1 ul of the cDNA reaction mix with blue dye (0.0032%) added to 19 ul qPCR master mix with blue dye (0.0003%).

Figure 3A:
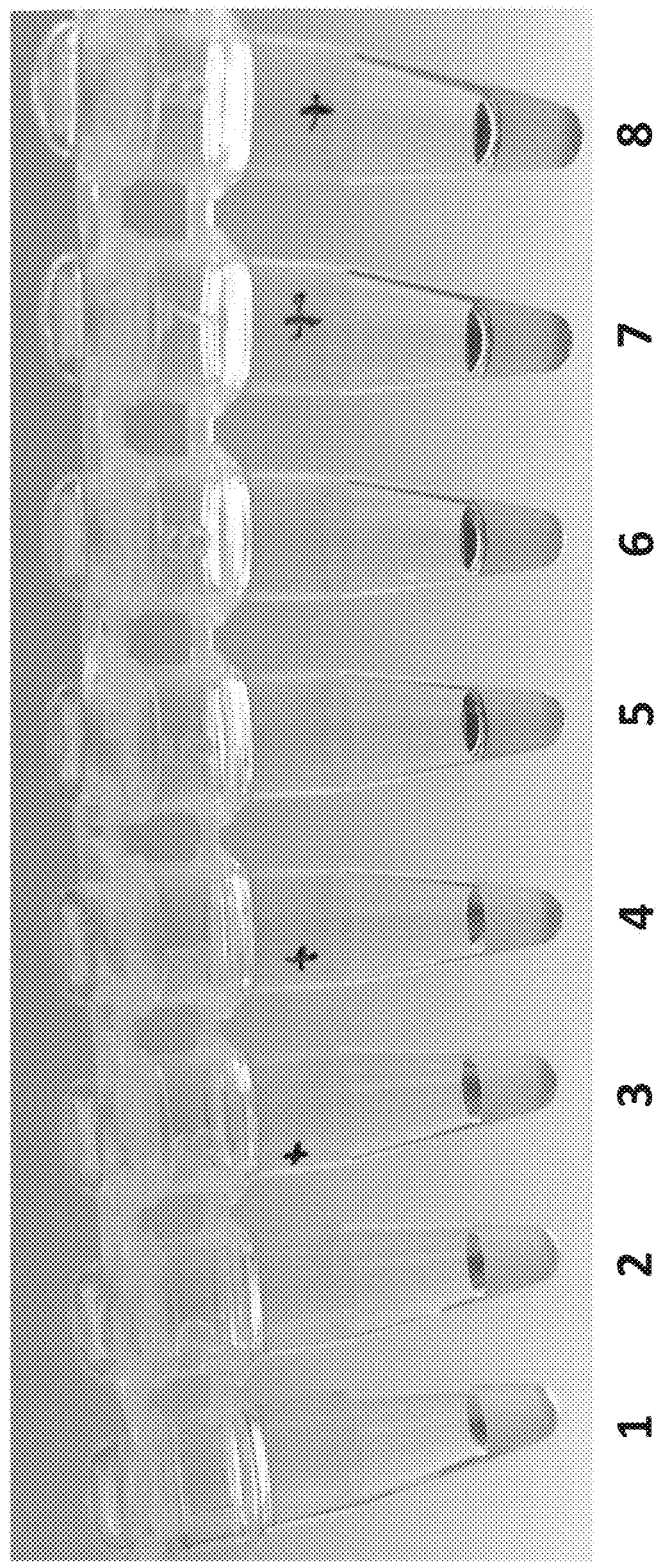
FIG. 3A shows the result of adding 1 ul of a cDNA reaction mix containing 0.0032% xylene cyanol blue dye into 19 ul qPCR reaction mix. The addition of the cDNA reaction mix containing dye to the qPCR mix can be readily seen by the bead of concentrated dye at the bottom of the tube.
Figure 3B:
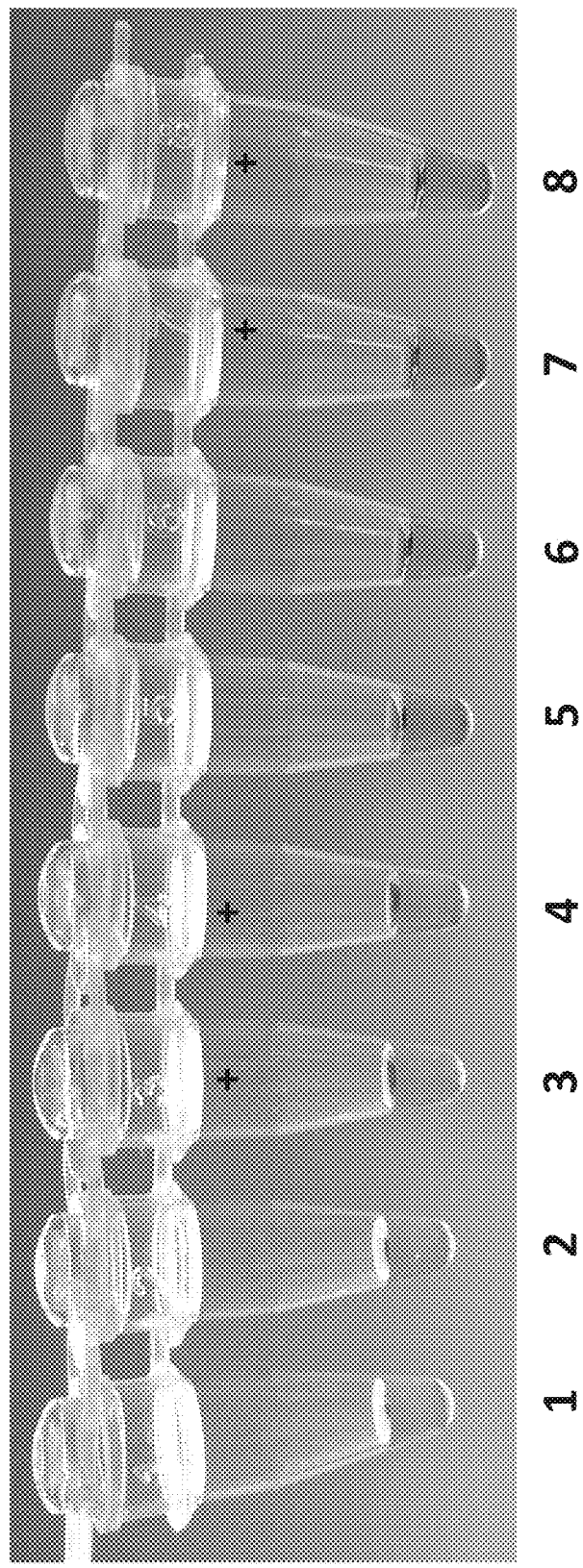

FIG. 3B shows the result of adding 1 ul of a cDNA reaction mix containing 0.0154% tartrazine yellow dye into 19 ul qPCR reaction mix with no dye or with 0.0003% xylene cyanol. The addition of the cDNA reaction mix can be readily detected by the bead of concentrated dye at the bottom of the tube.

From left to right:

Tubes 1 and 2 contain a cDNA reaction mix and qPCR master mix both without dye.

Tubes 3 and 4 contain a cDNA reaction mixture containing a yellow dye added to qPCR master mix without dye.

Tubes 5 and 6 contain a qPCR reaction mix with blue dye into which DNA from the cDNA reaction mix with no dye has been added.

Tubes 7 and 8 contain a cDNA reaction mix with yellow dye added to a qPCR reaction mix containing blue dye.

Figure 3C:
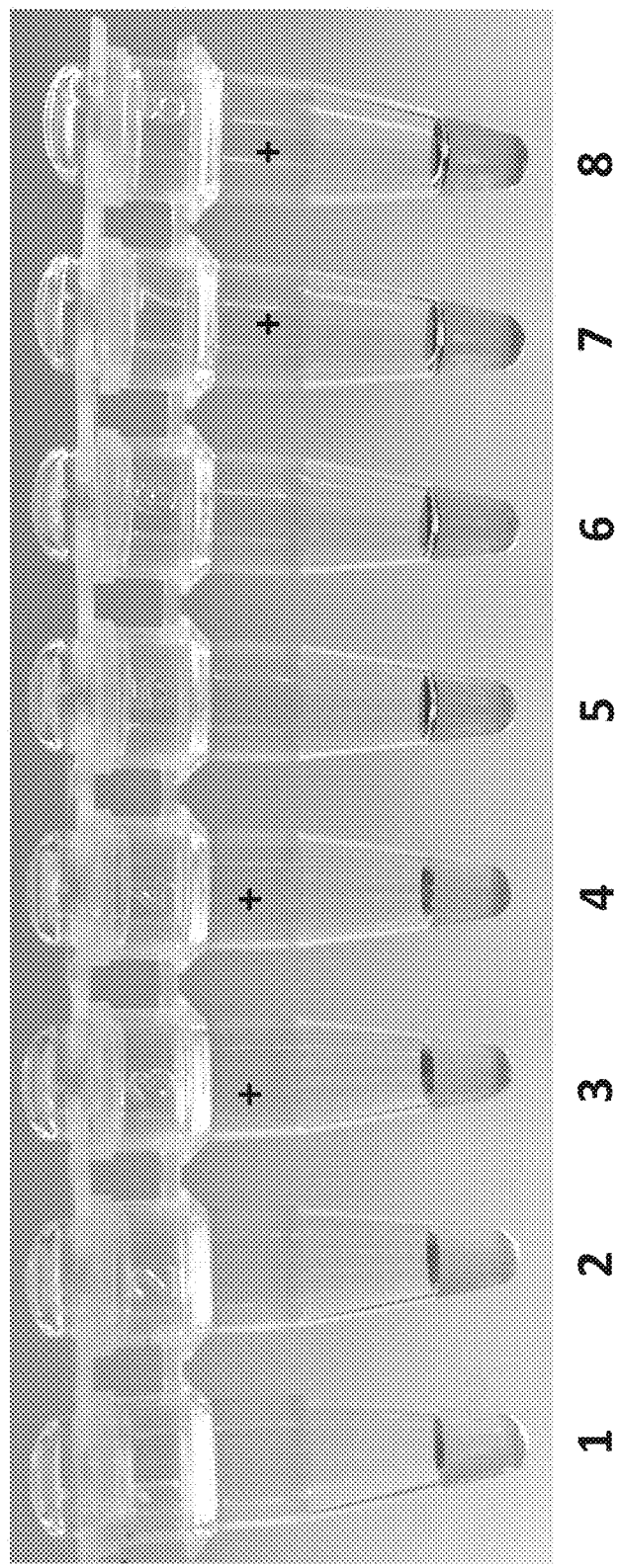

FIG. 3C shows the result of adding 1 ul of a cDNA reaction mix into a qPCR reaction mix where the cDNA reaction mix contains 0.0077% tartrazine yellow dye and 0.0077% xylene cyanol blue dye to give a green color. The addition of 1 ul of the cDNA reaction mix with dye to 19 ul qPCR reaction mix without dye can be readily seen by the bead of concentrated dye at the bottom of the tube.

From left to right:

Tubes 1 and 2 (no dye in the cDNA reaction mix and no dye in qPCR master mix).

Tubes 3 and 4 contain cDNA reaction mix with dye mix added to qPCR master mix without dye.

Tubes 5 and 6 contain cDNA reaction mix with no dye added to a qPCR mix with blue dye (0.0003%).

Tubes 7 and 8 contain cDNA reaction mix with dye mix added to qPCR master mix with blue dye (0.0003%).

Figure 4A:
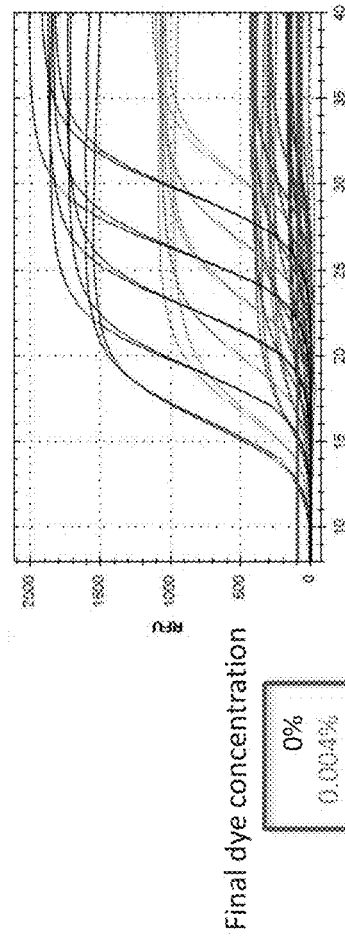
Figure 4B:
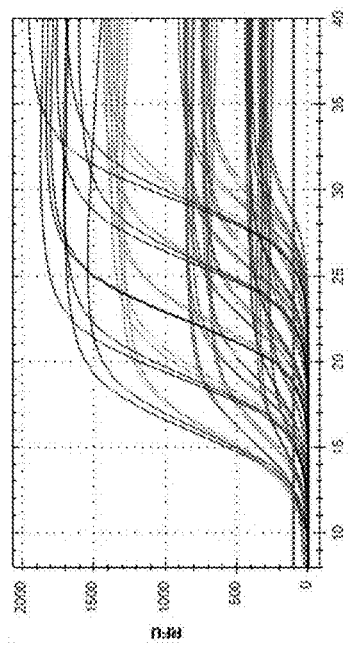
Figure 4C:
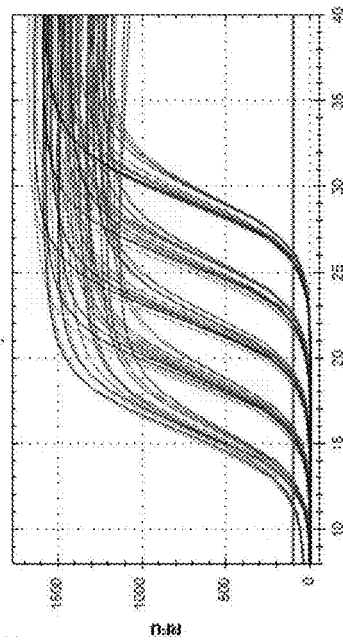
Figure 4D:
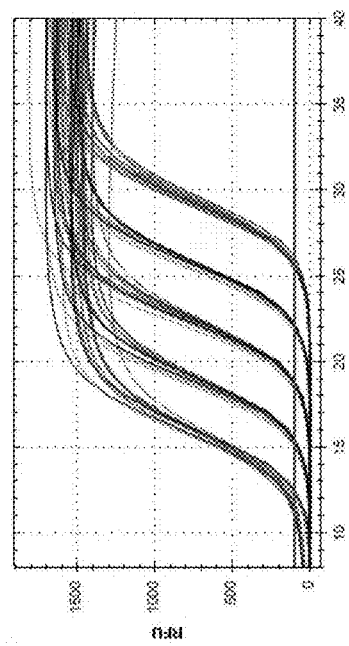

FIG. 4A-4D shows a measure of inhibition by adding various concentrations of dye directly into the qPCR reaction (FIG. 4A) and (FIG. 4C) and into the cDNA reaction containing reverse transcriptase (FIG. 4B) and (FIG. 4D). The concentrations of dye tested are 0.004%, 0.008%, 0.012%, 0.016%, 0.023%.

FIGS. 4A and 4B shows the effects of varying concentrations of xylene cyanol on qPCR (FIG. 4A) and reverse transcription (FIG. 4B).

FIGS. 4C and 4D shows the effects of a mixture of xylene cyanol and tartrazine on qPCR (FIG. 4C) and reverse transcription (FIG. 4D).

Figure 5:
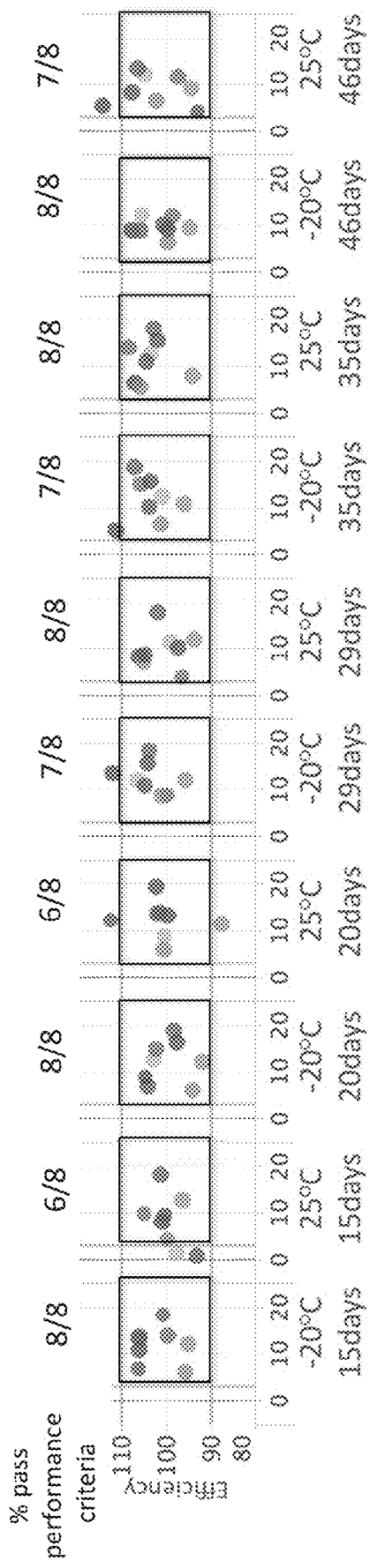
Figure 5:
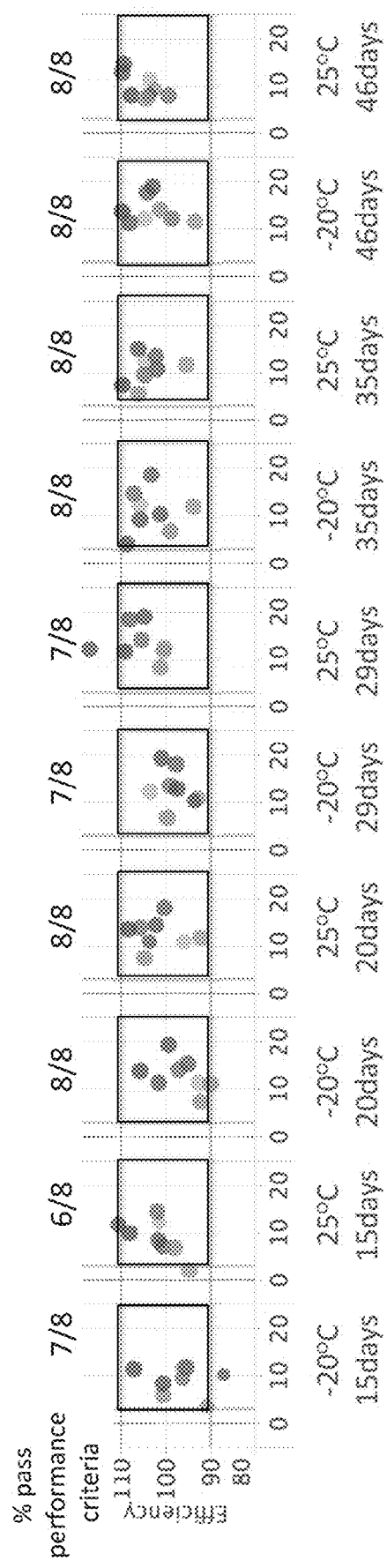

FIG. 5 shows that the quality (size of dot, see for example Hall, et al. (2013) PLOS One 8: e73845), sensitivity as denoted by the coordinates of the dot (where the x-axis is the ΔCq and Y-axis is the machine calculated efficiency value), and the efficiency of qPCR (Y-axis value) following cDNA synthesis using a cDNA synthesis mix with or without dye to which single strand nucleic acid is added, the cDNA synthesis mix being stored at −20° C. or 25° C. for 15-46 days prior to cDNA synthesis. The presentation of the data in this way is described by Patton G. C., et al, (2017) NEB expressions, Issue I, 2-5.

DETAILED DESCRIPTION OF EMBODIMENTS

Unless otherwise defined, all technical and scientific terms used herein have the same meaning as commonly understood by one of ordinary skill in the art to which this invention belongs. Still, certain elements are defined for the sake of clarity and ease of reference.

The term "dye" is exemplified here by single colors which are the result of single dyes or combinations of dyes. Wherever the use of a visually detectable dye is described, it should be understood the dye is observable as a specific color (e.g., blue, green, yellow or cyan, etc.) by eye, although the color emitted by the dye may be due to fluorescence. Colored dyes suitable for use in the mixtures and methods of the invention include xylene cyanol, tartrazine and orange G, which may be used alone or in combination.

The term "reverse transcriptase mixture" refers to an aqueous solution that contains a reverse transcriptase and a colored dye as described herein and may also contain one or more of the following: a buffer, glycerol or equivalent, dNTPs, adaptors, RNAse inhibitors, and primers (e.g. random primers). The reverse transcriptase mixture may contain any reagent, except the target nucleic acid, used in a cDNA reaction whether it be just reverse transcription or whether it includes template switching or other methods in which a nucleic acid is reverse transcribed for purposes of quantitation, modification, enrichment, amplification and/or sequencing. When the reverse transcriptase mixture contains one or more reagents for cDNA synthesis (except the target nucleic acid) it may be identified herein as a "cDNA synthesis mix" or "supermix". In some embodiments the activity of reverse transcriptase in a reverse transcriptase mixture may be stable (i.e., does not lose more than 10% of its activity) for a period of time (e.g., one month, six months or one year) in storage in a frozen form, e.g., at a low temperature (which may be below 5° C., e.g., at approximately −20° C.). In the examples, a thermostable reverse transcriptase commercially available having the name Luna® RT (New England Biolabs, Ipswich, MA) was used. Although a single reverse transcriptase is exemplified below, other transcriptases that are commercially available such as SuperScript™ RT (ThermoFisher Scientific, Waltham, MA), iScript™ RT (BioRad, Hercules, CA), WarmStart® RTx and ProtoScript® RT (New England Biolabs, Ipswich, MA).

A "reverse transcriptase" (RT) is any enzyme capable of copying a single strand nucleic acid (e.g. RNA or DNA) to produce a complementary single strand DNA (cDNA). Reverse transcriptases are frequently derived from viruses. Examples include Mouse murine leukemia virus (MMLV), retroviruses such as HIV, Avian myeloblastosis virus (AMV). Reverse transcriptases also include Group II intron reverse transcriptase. Included in this description are variants and mutants of the reverse transcriptases described herein. As described above, examples of commercial reverse transcriptases include Luna RT, ProtoScript RT, SuperScript RT, iScript RT, and WarmStart RTx.

The compositions described herein are non-naturally occurring in that they do not exist in nature. In this context, the term "non-naturally occurring" refers to a colored dye or to a protein that has an amino acid sequence and/or a post-translational modification pattern that is different to the protein in its natural state. For example, a non-naturally occurring dye is one that is made by synthetic chemistry and is not found in nature. A non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence but that that is at least 80%, at least 85%, at least 90%, at least 95%, at least 97%, at least 98% or at least 99% identical to a naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. The non-naturally occurring protein may include a fusion protein in which two peptides are fused together in an unnatural fusion formed for example from an enzymatically active peptide and a substrate binding peptide.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; e) a combination that is in a form that not found in nature, e.g., dried, freeze dried, crystalline, aqueous; and/or d) a combination that contains a component that is not found in nature. For example, a preparation may contain a buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

A nucleic acid that is a template for reverse transcriptase is a single strand DNA or RNA. Where the template is a single strand RNA, the cDNA synthesis mix, or cDNA reaction mix may include reagents for template switching including oligonucleotides that may be used as adaptors which can be added using the template switching properties of the reverse transcriptase.

The mixtures, kits, and methods described herein may comprise a buffer or buffering agent. As used herein, the term "buffering agent", refers to an agent that allows a solution to resist changes in pH when acid or alkali is added to the solution. Examples of suitable non-naturally occurring buffering agents that may be used in the mixtures, kits, and methods of the invention include, for example, Tris, HEPES, TAPS, MOPS, tricine, or MES.

Surprisingly it was found here that reverse transcriptases can tolerate significantly higher concentrations of colored dyes than can Taq polymerase, as determined by qPCR, without significantly changing its ability to synthesize cDNA, as illustrated in FIG. 4A-4D. This effect is shown with 2 dyes used individually (blue dye or a yellow dye) and also 2 dyes used in combination to create a third color (green). As illustrated in the Examples, the activity of reverse transcriptase in a cDNA reaction was not inhibited by colored dye(s) at a concentration of 0.023% (w/v), whereas the activity of Taq polymerase was significantly inhibited by the dye(s) at lower concentrations of only 0.004% (w/v). The new found use of higher concentrations of a single visible color in reverse transcriptase reactions provides a simple single-color method of assessing the fluid volume of reagents (e.g. in pipette tips) and/or tracking the addition of reagents by eye without requiring the use of an optical device. This type of tracking is distinct from and does not include mixing two different colors from two different solutions and then looking for a color changes after the 2 colors are mixed (see for example WO 2011/039425). Also excluded are reactions which cause a color change in a visible dye to denote that the reaction has occurred (e.g. a pH-dependent color change), such as described in U.S. Pat. No. 9,034,606. In the mixtures and methods described herein, a single dye is preferably used at significant concentrations (e.g. up to 1% (w/v)) in the presence of one or more enzymes where upon dilution the dye remains detectable and is non-toxic to the enzymes in the mixtures.

A reverse transcriptase mixture may comprise a reverse transcriptase and a colored dye at a concentration in the range of 0.003% to 1% (w/v), where the concentration of colored dye in the mixture may be inhibitory to Taq polymerase. The colored dye may be present at a concentration of at least 0.01% or 0.02% (w/v), and/or may be present at a concentration of up to 0.03%, 0.05%, or 1% (w/v); for example, the colored dye may be present in a concentration range of 0.01% to 1% (w/v), 0.01% to 0.05% (w/v) or 0.01% to 0.03% (w/v). The color of the dye in the reverse transcriptase mixture (or in the cDNA synthesis mix or cDNA reaction mix) may be used to track transport of the mixture from one vessel to another, by eye. For example, a mixture described herein may be transported from one vessel (e.g. sample tube) to another in one or more pipette tips. The color of the dye may be used to ensure that the mixture has been successfully added to a receiving/recipient mixture, e.g., by observing a "bead" of color at the bottom of the recipient mixture. In some embodiments, the reverse transcriptase mixture is used in a method that involves combining a defined amount of the mixture (e.g., an amount in the range of 1-5 ul) with other necessary reagents (e.g., reverse transcription buffer, single strand nucleic acid template, dNTPs, etc.) to form a cDNA synthesis mix such that when this is added to a nucleic acid, a cDNA reaction mix is formed to produce cDNA. Aliquots of the cDNA reaction mix may be transferred into a PCR mix that may comprise PCR primers, Taq polymerase, dNTPs and other necessary reagents for PCR. Using the colored primary mix to color the receiving mixes serially and/or in parallel as needed confirms to the user that the defined amount of the mixture has been transported and that the mixture has been successfully added to the PCR mix, to produce a PCR reaction and PCR product. The embodiments include observing transport of the defined amount of the mixture and confirming that the mixture has been successfully added to a reaction buffer. Although the dye in the reverse transcriptase mixture may be at a concentration that inhibits Taq polymerase, in one embodiment, by the time that it is added to the PCR reaction the dye has been diluted at least 2×, 5×, at least 10×, or at least 20× and, as such, is not at a concentration that inhibits Taq polymerase in the PCR reaction. In these circumstances, the concentration of the dye in the PCR reaction may be above 0.0026%, and preferably below 0.007% (w/v).

When the concentration of a single dye in a reagent of the invention is sufficiently high, pipetted samples of the reagent and the presence of the added reagent in a reaction vessel can be readily detected by the naked eye. Moreover, a sufficient concentration of dye permits an iterative process whereby the sample containing dye can be moved through various dilutions that occur in sequential reaction mixes while being visually detectable at each dilution.

In embodiments of the invention, dyes such as xylene, tartrazine, orange G and coccine can be used above a concentration of 0.0026% w/v to concentrations as high as 1% w/v in a mixture containing a reverse transcriptase. The concentration of the dye may be (or may be at least) 0.003%, 0.004%, 0.005%, 0.006%, 0.007%, 0.008%, 0.009%, 0.01%, 0.05%, 0.07%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 1% (w/v), or any value therebetween. In some embodiments, the concentration of dye may be up to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, or 1% (w/v), or any value therebetween. In one embodiment, the concentration of the dye is 0.003%-0.13% in a 1× reverse transcriptase mix. In another embodiment, the dye is present at a concentration of 0.006%-0.15% in a 2× reverse transcriptase mix. In another embodiment, the dye is present at a concentration of 0.015%-0.65% in a 5× reverse transcriptase mix and in another embodiment, the dye is present at a concentration of 0.03%-1% in a 10× reverse transcriptase mix. In one embodiment, 100% dye corresponds to 1 gm/100 ml.

In some embodiments, a cDNA synthesis mix is formulated where the dye concentration is no more than about 0.04%, for example, the dye concentration is (or is at least) 0.003%, 0.005%, 0.007%, 0.01%, 0.02%, or 0.03%. If the dye is fluorescent, effective concentrations may be higher than for visible colored dyes.

In embodiments of the invention, the reverse transcriptase may be combined with a visible dye at any of the above defined concentrations, where the reverse transcriptase may be present at any desired concentration for example at 2-40 U/ul in the 1× buffer, 4-80 U/ul in a 2× buffer, 10-200 U/ul in a 5× buffer and 20-400 U/ul in a 10× buffer where the buffer may be suitable as a storage buffer for the reverse transcriptase mix. Glycerol or equivalent may be included in the reverse transcriptase mix, including the cDNA synthesis mix. In some embodiments, the reverse transcriptase, with the dye, may be combined with as much as 80% (v/v) of glycerol or equivalent, to form a homogeneous colored preparation. In an embodiment, the reverse transcriptase mix may include 5%-80% (v/v) glycerol or equivalent. For example, glycerol or equivalent may be included in the mix at a concentration of (or at least) 5%, 10%, 15%, 20%, 30%, 40%, 50%, 60%, 70% or 80% (v/v) glycerol or equivalent or any concentration in between. For example, a 1× reverse transcriptase mix or cDNA synthesis mix may contain 5%-60% v/v glycerol or equivalent, and a 2×, 5× and 10× reverse transcriptase mix or cDNA synthesis mix may contain 5%-80% glycerol or equivalent.

When a sample from the cDNA reaction mix is introduced into a PCR mix (such as a qPCR mix), then the final concentration of the dye in the PCR (e.g. qPCR) reaction mix is preferably less than 0.007%, 0.005%, 0.004% or 0.003% (w/v).

In embodiments, a homogenous colored preparation may be provided that contains all the required reagents to perform cDNA synthesis including reverse transcriptase. This preparation is also identified herein as a "cDNA synthesis mix". The reagents may be contained in a storage buffer, a mastermix, or in a reaction buffer according to the needs of the user. This solution may be added to single strand nucleic acid to synthesize cDNA, prior to an optional second step which might for example be qPCR or PCR or second strand cDNA synthesis or digital PCR or an isothermal amplification reaction such as rolling circle amplification (RCA), strand displacement amplification (SDA), helicase dependent amplification (HDA), loop-mediated isothermal amplification (LAMP), or any other amplification reaction generally known in the art.

An advantage of combining a concentrated reagent with the colored dye in a primary mix containing glycerol or equivalent is that when pipetted into a second solution, it temporarily forms a colored bead at the bottom of the reaction vessel (e.g. sample tube) which is readily detectable by eye thus informing the user that a successful transfer of the reagent has occurred (see for example, FIGS. 3A-3C). The bead visible in the bottom of the tube diffuses in time throughout the solution, which makes detection of the colored reagent (reverse transcriptase mix or cDNA synthesis mix) in the cDNA reaction mix, simple, reliable and quick, even when the final solution concentration is low.

If the reverse transcriptase is in a mix containing buffer and dye, the dye will travel with the reverse transcriptase in a visibly detectable manner into subsequent uncolored reaction vessels. For example, when the user adds a sample of reverse transcriptase mix, comprising the reverse transcriptase with dye, into a cDNA synthesis mix without template single strand nucleic acid (also referred to as a supermix), the dye in the reverse transcriptase mix will be diluted. If the supermix is then added to template single strand nucleic acid in a solution to enable cDNA synthesis to occur, further dilution of the dye will occur. If an aliquot of the cDNA reaction mix containing the cDNA product and diluted dye is transferred to a qPCR buffer plus Taq polymerase, the dye will be further diluted. If the initial concentration of dye is sufficiently high, it remains simple to visually detect the transfer of fluid from reaction vessel to reaction vessel (e.g. tube to tube) and to confirm visually the correct volume of liquid transferred between reaction tubes (e.g. via pipette, such as in a multi-channel pipette). The initial concentration of dye in the reverse transcriptase mix alone, or in the supermix, or in the cDNA reaction mix, may require a 10 fold or 20 fold dilution into a subsequent mixture, hence the advantage of starting with a relatively high concentration of dye in the reverse transcriptase mix or supermix. Detection can be facilitated if the preparation containing the dye also contains an inert but dense material such as glycerol or equivalent. Transfer of the solution containing the dye and an inert but dense material such as glycerol or equivalent into a solution that does not contain the dye, or contains the dye at a much lower concentration, results in the temporary formation of a colored bead containing the transferred reagent at or towards the bottom of the tube as shown in FIG. 3A-3C.

In one embodiment, single strand nucleic acid (e.g. DNA or RNA) is added to the mix containing a reverse transcriptase, a visible dye and glycerol or equivalent (the reverse transcriptase mix or cDNA synthesis mix/supermix) to form a cDNA reaction mix. An aliquot of the resultant cDNA reaction mix can then be added into a subsequent reaction mix such as a PCR reaction mix (for example, qPCR). The transfer can be confirmed by visually-detecting the presence of a colored bead in the PCR (e.g. qPCR) tube.

Several types of mix are used herein with dyes where the dyes do not detectably inhibit reverse transcriptase enzyme activity. These mixes include among other possible reagents, the following:
(a) reverse transcriptase and dye in a buffer ("reverse transcriptase mixture");
(b) reverse transcriptase, dye, dNTPs, primers (e.g. random primers), and buffer ("cDNA synthesis mix" or "supermix");
(c) reverse transcriptase, dye, dNTPs, primers (e.g. random primers), single strand nucleic acid, and buffer ("cDNA reaction mix");
(d) reverse transcriptase, dye, dNTPs, primers (e.g. random primers and/or specific primers), cDNA, Taq polymerase, and buffer (PCR reaction mix (e.g. qPCR reaction mix)) where (a) (b) or (c) may be a primary mix and (d) is a receiving mix. If (a) is the primary mix than (b), (c) and (d) are receiving mixes. If (a) and (b) are the primary mixes, then (c) is the first receiving mix and (d) is the second receiving mix.

Figure 1B:
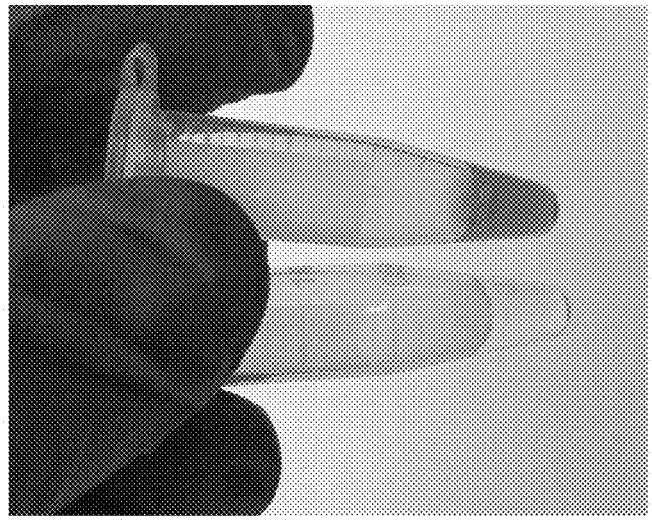
Figure 1A:
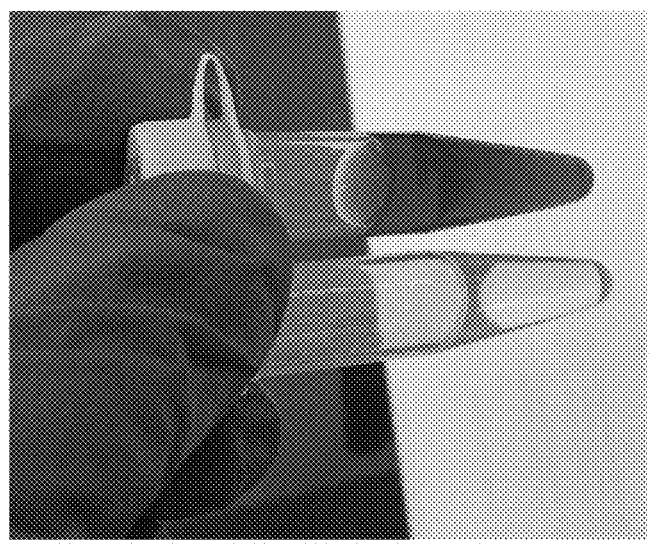
Figure 2A:
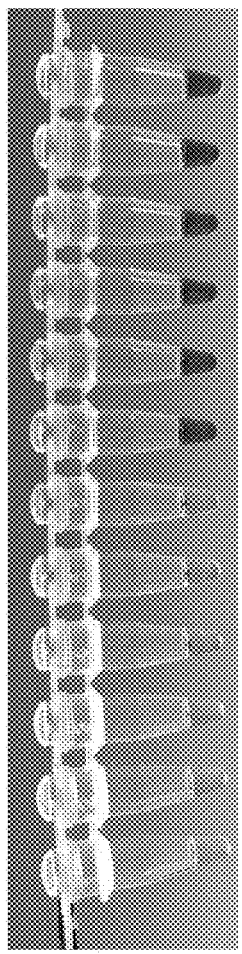
FIG. 2A-2G shows sample tubes and pipette tips with and without dyes for assessing the presence of reagents and the volume of fluids in each pipette tip using several dyes.
Figure 2C:
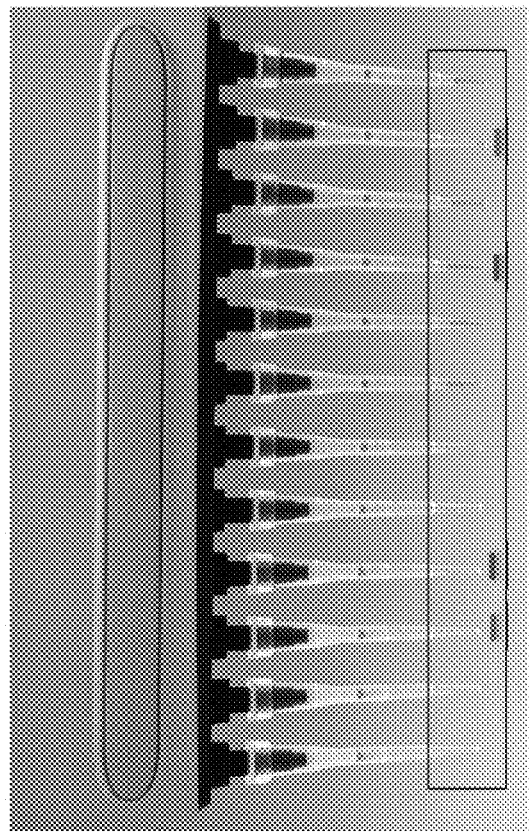
Figure 2B:
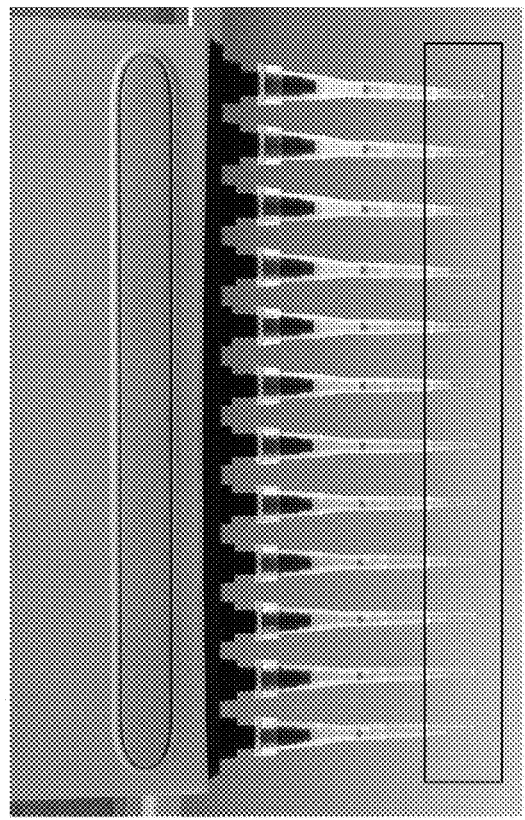
Figure 2D:
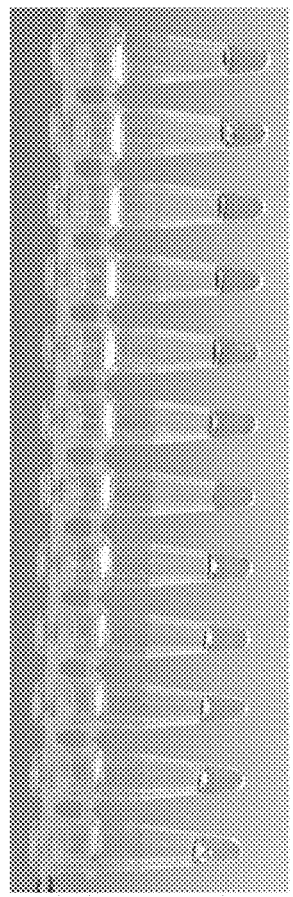
Figure 2E:
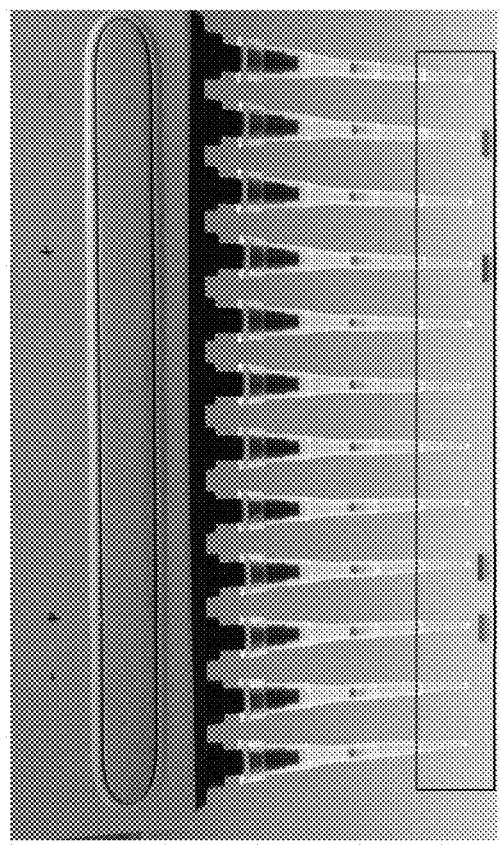
Figure 2F:
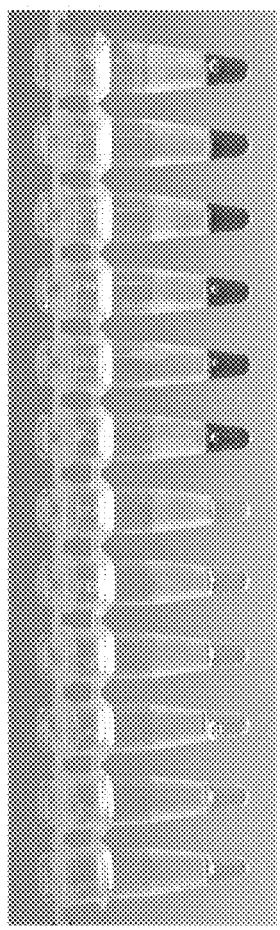
Figure 2G:
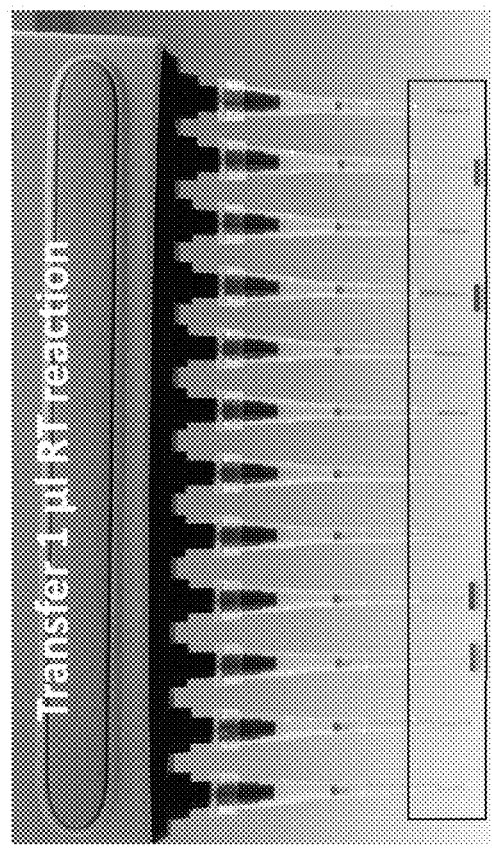

The figures show the intensity of the color of: xylene cyanol at 0.016%. (FIGS. 1A-1B) and at 0.0032% (FIG. 2A-2C); 0.0154% tartrazine dye (FIG. 2D); and 0.0077% of each of xylene cyanol and tartrazine dyes (FIG. 2F). FIG. 3A-3C shows how 1 ul of a dye-containing reaction mix added to a tube containing 19 ul of a second solution containing no dye or a dye at a concentration at least 10 fold less than the reaction mix can form a temporary visually-distinguishable bead at the bottom of the tube.

Also provided by this disclosure is a kit for practicing the subject method, as described above. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

All publications, patents, and patent applications mentioned in this specification are herein incorporated by reference to the same extent as if each individual publication, patent, or patent application was specifically and individually indicated to be incorporated by reference. This includes U.S. Provisional Application 62/637,029 filed on Mar. 1, 2018.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1: The Effect of Dyes on cDNA Synthesis and on qPCR

Dyes at a concentration of 0.0003% in a qPCR mix were found not to inhibit Taq polymerase in a qPCR mix in a manner that was detrimental to the reaction. 5-log dilutions of Jurkat total RNA (1 ug, 100 ng, 10 ng, 1 ng, 100 pg) were used as the template RNA for cDNA synthesis using a commercially available thermostable reverse transcriptase (Luna RT). The product of cDNA synthesis which used random primers and dT primers resulted in a library of cDNA molecules after incubation at 25° C. for 2 minutes, 55° C. 10 minutes, and 95° C. 1 minute. 1 ul cDNA library was added to a qPCR reaction mixture containing Taq polymerase (Luna® Universal qPCR Master Mix (New England Biolabs, Ipswich, MA)) and specific primers were added to detect glyceraldehyde 3-phosphate dehydrogenase (GAPDH) in the presence of xylene cyanol at a final concentration of 0%, 0.004%, 0.008%, 0.012%, 0.016%, or 0.023%, or Xylene cyanol and tartrazine both in the concentration range described above.

The presence of increasing amount of xylene cyanol in the qPCR reaction led to higher Cq value, indicating stronger inhibition of Taq polymerase by xylene cyanol. FIG. 4A and FIG. 4C shows the inhibitory effect of xylene cyanol and the mixture of 2 dyes on qPCR.

Dyes at a concentration of 0.023% do not inhibit cDNA synthesis in the presence of a reverse transcriptase.

5-log dilutions of Jurkat total RNA (1 ug, 100 ng, 10 ng, 1 ng, 100 pg) were used as the template RNA for cDNA synthesis using Luna RT in the presence of xylene cyanol at a final concentration of 0%, 0.004%, 0.008%, 0.012%, 0.016%, or 0.023%, or Xylene cyanol and tartrazine both in the concentration range described above. The product of cDNA synthesis which used random primers and dT primers resulted in a library of cDNA molecules after incubation at 25° C. for 2 minutes, 55° C. 10 minutes, and 95° C. 1 minute. 1 ul cDNA library was added to a qPCR reaction mixture containing Taq polymerase and specific primers were added to detect GAPDH.

The presence of increasing amount of xylene cyanol in the cDNA reaction did not change the Cq value, indicating that no detectable inhibition of the reverse transcriptase occurred in the presence of xylene cyanol. FIG. 4B shows the inhibitory effect of xylene cyanol and FIG. 4D the mixture of 2 dyes on qPCR.

Example 2: Similar Performance and Stability of MMLV Mutant Reverse Transcriptase was Observed by 2-Step RT-qPCR with or without Xylene Cyanol in the cDNA Synthesis Storage Mix The cDNA synthesis storage mix contained Luna® RT, dNTP, oligos, buffer components in the presence of xylene cyanol (0.016%) or absence of xylene cyanol. The storage mix was maintained at −20° C. or 25° C. for various periods of time to determine stability. RNA from 5-log dilutions of Jurkat total RNA (1 ug, 100 ng, 10 ng, 1 ng, 100 pg) was added to aliquots of the storage mix after various time intervals to generate cDNA. Varying amounts of RNA input provided a measure of sensitivity of the cDNA synthesis and the capacity of the reaction to generate cDNA. After cDNA synthesis (25° C. for 2 minutes, 55° C. 10 minutes, and 95° C. 1 minute), 1 ul cDNA library were then evaluated by qPCR using eight specific primer sets to analyze 8 target RNAs that varied in abundance, length and % GC. qPCR detection was performed using Luna Universal qPCR Master Mix. Results were evaluated for efficiency and $\Delta C_q$, where $\Delta C_q$ measures low input detection and lack of no-template control (NTC) amplification ($\Delta C_q$=average $C_q$ of NTC−average $C_q$ of lowest input). Black box indicates target performance criteria (Efficiency=90-110%, $\Delta C_q \geq 3$). ⅞ means seven out of eight targets were inside the box and satisfy qPCR quantitative detection.

What is claimed is:

1. A method comprising:
   (a) combining:
      (i) a supermix that comprises a reverse transcriptase, one or more primers, a dye selected from xylene cyanol and/or orange G, the dye at a concentration of 0.01% to 1% (w/v), an inert high-density material, and no Taq polymerase; with
      (ii) RNA,
   to produce a cDNA synthesis mix;
   (b) incubating the cDNA synthesis mix for a period of time to produce a cDNA product;
   (c) combining an aliquot of the cDNA product with a receiving mix that comprises a Taq polymerase and a primer pair and does not contain a different dye, to produce a PCR mix,
   wherein the xylene cyanol and/or orange G is diluted in concentration by at least 5-fold by the receiving mix;
   and wherein a bead of the cDNA product forms at the bottom of the receiving mix;
   (d) visually observing the bead of the cDNA product;
   (e) thermocycling the PCR mix of step (c); and
   (f) detecting a reaction product of step (e).

2. The method of claim 1, wherein step (f) comprises quantifying the amount of reaction product produced in the thermocycling of (e).

3. The method of claim 1, wherein the xylene cyanol and/or orange G is diluted in concentration by at least 10-fold in step (c).

4. The method of claim 1, wherein the one or more primers include random primers.

5. The method of claim 1, wherein the inert high-density material is glycerol or an equivalent selected from the group consisting of glycerol, ficoll, polyethylene glycol, dextran or polysucrose and the concentration of the glycerol or equivalent in the supermix is in the range of 5% to 80% v/v.

6. The method of claim 5, wherein the supermix comprises at least 30% glycerol.

* * * * *